United States Patent
Asche et al.

[11] Patent Number: 6,010,505
[45] Date of Patent: Jan. 4, 2000

[54] SUPRA CONDYLUS BONE NAIL

[75] Inventors: Gernot Asche; Hans Erich Harder; Thomas Heinrich Anton Heinz; Klaus Hornberger; Reinhard Schnettler; Vilmos Vécsei, all of New York, N.Y.

[73] Assignee: Howmedica GmbH, Germany

[21] Appl. No.: 08/920,450

[22] Filed: Aug. 29, 1997

[30] Foreign Application Priority Data

Sep. 5, 1996 [DE] Germany ............... 296 15 482 U

[51] Int. Cl.[7] ................. A61B 17/56; A61B 17/58; A61F 2/30
[52] U.S. Cl. ............................................. 606/62
[58] Field of Search ................... 606/60, 62, 67, 606/72, 74, 86, 95, 96, 87, 53

[56] References Cited

U.S. PATENT DOCUMENTS

| | | | |
|---|---|---|---|
| 2,489,870 | 11/1949 | Dzus . | |
| 4,473,069 | 9/1984 | Kolmert | 128/92 B |
| 4,979,949 | 12/1990 | Matsen, II et al. | 606/53 |
| 5,035,697 | 7/1991 | Frigg | 606/67 |
| 5,041,115 | 8/1991 | Frigg et al. | 606/62 |
| 5,066,296 | 11/1991 | Chapman et al. | 606/64 |
| 5,201,735 | 4/1993 | Chapman et al. | 606/67 |
| 5,248,313 | 9/1993 | Greene et al. | 606/62 |
| 5,497,592 | 3/1996 | Boeshart | 52/699 |
| 5,573,536 | 11/1996 | Grosse et al. | 606/60 |
| 5,620,445 | 4/1997 | Brosnahan et al. | 606/63 |
| 5,735,536 | 4/1998 | Myers et al. | 280/7.13 |

FOREIGN PATENT DOCUMENTS

| | | |
|---|---|---|
| 0332857A1 | 9/1989 | European Pat. Off. . |
| 0355411A1 | 2/1990 | European Pat. Off. . |
| 0381462A | 8/1990 | European Pat. Off. . |
| 2699065A | 6/1994 | France . |
| 2729558A | 7/1996 | France . |
| 9517318 U 1 | 2/1996 | Germany . |
| 2290478 | 1/1996 | United Kingdom . |
| 9602203 | 1/1996 | WIPO . |

*Primary Examiner*—Michael Buiz
*Assistant Examiner*—Vy Q. Bui
*Attorney, Agent, or Firm*—Lerner, David, Littenberg, Krumholz & Mentlik, LLP

[57] ABSTRACT

A supracondylar bone nail has an elongated shank with a distal end and a proximal end and has two bends in the M-L plane. Both bends are in the same direction with screw holes between the distal tip of the nail and the first bend.

12 Claims, 2 Drawing Sheets

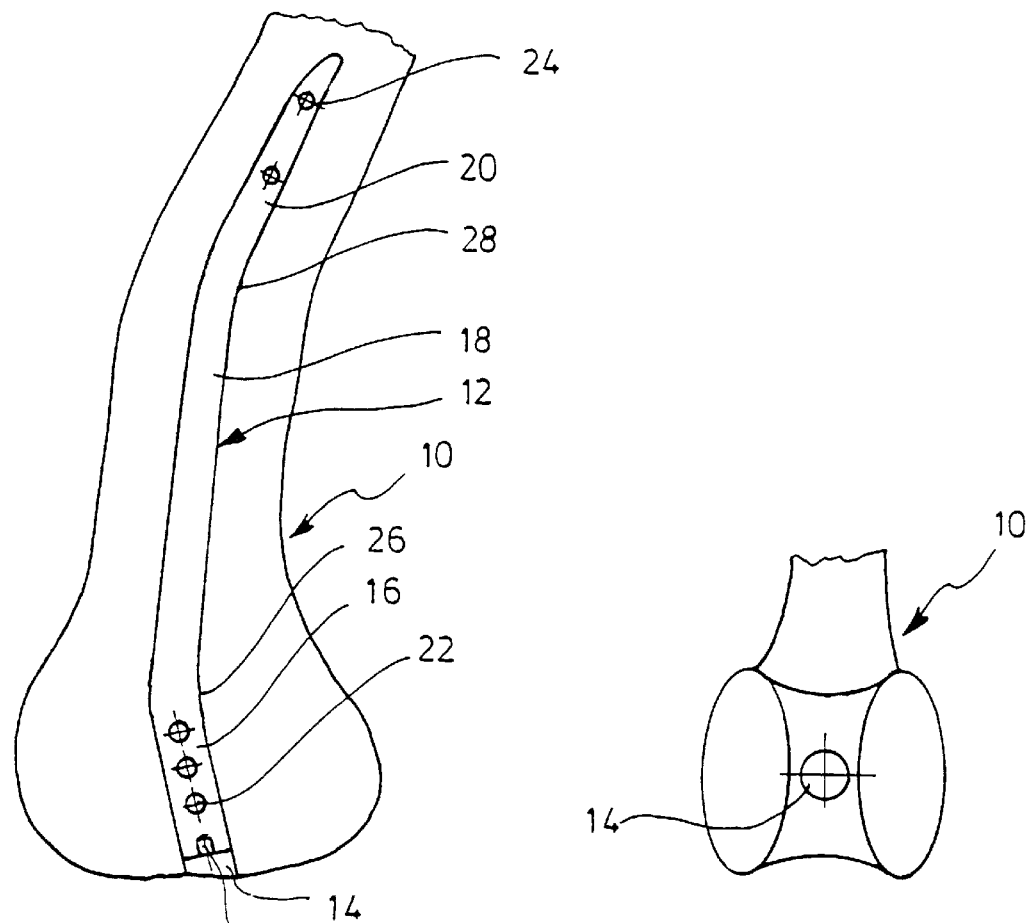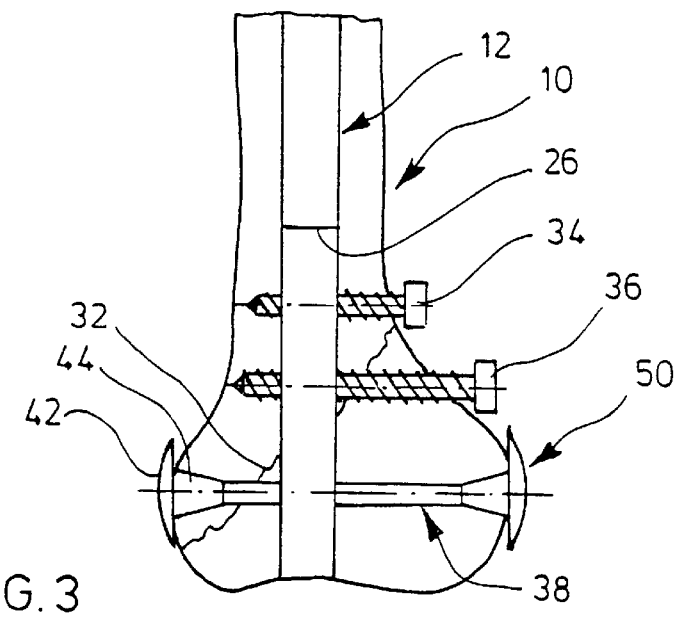

SUPRA CONDYLUS BONE NAIL

BACKGROUND OF THE INVENTION

The invention refers to a supra condylus bone nail.

Frequently, in cases of fractures of the femur bone, nails are applied which are driven into the intramedullary bone canal from proximal. It is also known to apply so-called locking nails which have transverse bores to be fixed on both sides of the fracture. Fractures in the condylus area of the bone necessitate a very long bone nail. Furthermore, the danger exists that the bone is pierced through in the area of the condylus by which cartilage is damaged.

OBJECTS OF THE INVENTION

An object of the invention is a supra condylus bone nail.

Another object of the invention is a method of repairing a fracture of a femur with a particular locking nail of the invention.

SUMMARY OF THE INVENTION

The bone nail according to the invention has an elongated shank which is relatively short if compared with known femur nails. The maximum length is for example 230 mm. The bone nail according to the invention is driven into a bore which ends at the distal end between the condylii and which follows the intramedullary canal. For the drilling of the bore and the insertion of the nail it is necessary to bend the knee and to laterally displace the patella. For the surgical operation this does not meet any obstacle. In view of the function of the knee the position of the bore is not critical since it is located remote from the sliding areas of the condylii on the plateau of the tibia.

According to the invention the bone nail includes two bends. The first begins at a distance from the distal end of about a quarter or a third of the length of the nail. The angle for example is 8°. The second bend begins in the last third of the nail length if looking from the distal end and has approximately an angle of 3° Both bends are lying in a plane parallel to the sagittal plane of the human body. Furthermore, the nail according to the invention has transverse bores in the distal and the proximal portion, with the bores extending transverse to the mentioned plane wherein the nail is bent. The bores are adapted to accommodate bone screws.

The bone nail according to the invention can be applied to fractures in the condylus area, with at least one screw being adapted to fix segments of the fracture in the distal area of the nail.

The diameter of the nail according to the invention which is approximately between 10 and 12 mm may be held constant for different lengths. Preferably, according to an embodiment of the invention a set of bone nails can be provided having the same diameter, however, a different length, with the length difference occurring only in the proximal portion behind the second bend while the remaining portion is approximately 120 to 130 mm if looking from the distal end and remains substantially constant.

According to another embodiment of the invention, the frontal side of the proximal portion of the shank has a skid-shaped flattening. This facilitates the driving and sliding in of the nail and avoids undesired damage to the bone.

According to another embodiment of the invention the shank is solid. Therefore, it is extremely stable in view of rotational and bending forces.

In order to allow application of a condylus screw in case of a fracture of the condylus portion, an embodiment of the invention provides that the condylus screw has a nut which is threaded onto a threaded portion of the shank of the condylus screw. Nut and head of the screw can be relatively thin. By means of such a condylus screw, segments of the fracture can be effectively compressed and retained at the nail.

The shank of such a condylus screw is preferably smooth. According to an embodiment of the invention the shank of the condylus screw is conically enlarged toward the end of the shank, and the nut includes a conical extension wherein an inner thread is formed to accommodate the threaded portion of the screw shank.

For the guidance of the condylus screw, in particular for threading the nut on the screw shank, an embodiment of the invention provides that the shank and shank head have an axial throughbore. A guiding lance may be threaded through the throughbore which allows a threading of the nut.

BRIEF DESCRIPTION OF THE DRAWING

The invention is explained in more detail with accompanying drawings.

FIG. 1 shows diagramatically the distal portion of a femur including a bone nail according to the invention.

FIG. 2 shows a bottom view of the femur of FIG. 1.

FIG. 3 shows a front view of the distal portion of a femur with a bone nail according to the invention.

DESCRIPTION OF THE PREFERRED EMBODIMENTS

Figure 4:
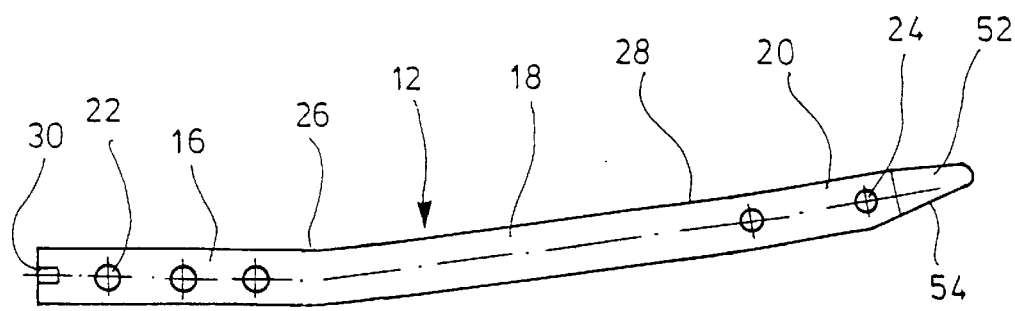
FIG. 4 shows a lateral view of the bone nail according to the invention.

In FIG. 1 the distal portion of a femur 10 is shown which accommodates a bone nail 12. The bone nail 12 is inserted through a bore 14 which is made from below the condylus retrograde (see FIG. 2).

In a plane parallel to the sagittal plane, the bone nail 12 which is solid and made of body compatible metal or metal alloy has a distal portion 16, an intermediate portion 18 and a proximal portion 20. Distal portion 16 and proximal portion 20 have three transverse bores 22 and two transverse bores 24, respectively. Between the portions 16, 20 a first bend 26 is provided with an angle of about 8°. A weaker bend is located between portion 18 and portion 20 as shown at 28. This bend has an angle of approximately 3°.

At its distal end, the bone nail 12 has diametrically opposed recesses 30 for the engagement of a driving instrument. Furthermore, the distal end may have an axial threaded bore (not shown). It also serves for the engagement with a driving or retracting instrument. In FIG. 3 it can be seen that the condylus portion of the femur 10 has a oblique fracture. The fracture line is designated with 32. Two bone screws 34, 36 having a drill tip are extended through two of the three transverse bores 22 and serve for the fixation of the bone nail 12 in the femur, with the lower screw 36 penetrating both segments of the fracture. A particular condylus screw 38 is extended through the distal transverse bore 22. The structure of the screw is explained in more detail with FIGS. 5 and 6. The condylus screw 38 has a thin smooth shank 40 which conically enlarges towards a head 42 as shown at 44. The head 42 is relatively thin and has a large diameter. The head 42, furthermore, has an inner hexagon 46 for a corresponding rotary tool. At the free end shank 40 has an outer threaded portion 48.

Figures 5, 6:
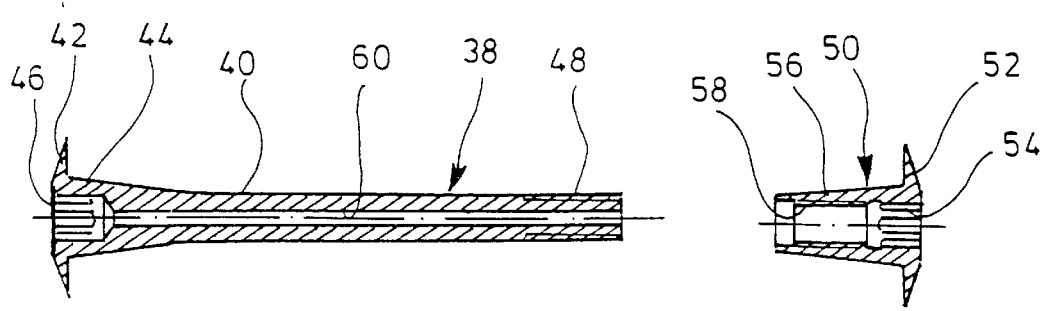
FIG. 5 shows a cross-section through a condylus screw for a bone nail of FIG. 4.
FIG. 6 shows a cross-section through a nut for the screw of FIG. 5.

A nut 50 in FIG. 6 has a flat head 52 similar to head 42 and an inner hexagon 54. A conical extension 56 joins to head 52 which is hollow and has an inner threaded portion 58 by which nut 50 can be threaded onto a threaded portion 48 of the condylus screw. As can be seen in FIG. 5, shank 40 and also head 46 are provided with a throughgoing axial bore 60 for the accommodation of a guiding lance.

As can be seen in FIG. 3 by means of the condylus screw shown in FIGS. 5 and 6 a compression force can be exerted onto the fracture segments. The diameter of shank 40 is such that it can be extended through the bores 22 with relatively small clearance.

In FIG. 4 the bone nail 12 is more clearly illustrated as to the dimensions thereof. It can be seen furthermore that the proximal end of nail 20 is pointed as shown at 52. Furthermore, it has a flattening 54 frontally faced which forms a skid for the introduction of nail 12. It is again mentioned that the nail 12 may have different lengths. From the distal end up to the bend 28 all nails have the same length independent of their total length. Merely the portions between bend 28 and the proximal end in a set of nails will have different lengths. The diameter of nail 12 is constant for all lengths.

We claim:

1. A supra condylus bone nail of body-compatible material having an elongated shank with distal portion and a distal end and a proximal portion and a proximal end sized and configured to be inserted from the distal end of a femur from below the condylus, said shank having a first bend spaced from said distal end lying in a first plane parallel to the medical plane of the human body, and a second bend spaced a greater distance from said distal end than said first bend and lying in said first plane, said proximal portion having at least one proximal transverse bore for a bone screw and said distal portion having at least one distal transverse bore located between said distal end and said first bend a condylus screw having a first part and a second part, said first part extending into said condylus in a medial-lateral direction from a first side thereof and having a length sufficient to extend through the distal transverse bore in said nail, said second part extending into said condylus in a medial-lateral direction from a second side thereof, said first and second parts having ends operatively coupled in a manner to compress a fracture in the condylus area of the bone.

2. The bone nail of claim 1, wherein said shank is solid.

3. The bone nail of claim 1, wherein said distal portion has three transverse bores.

4. The bone nail of claim 1, wherein said first part of said a condylus screw having a head and said second part having a nut adapted to be threaded onto a threaded portion of the shank of said screw, said nut having a head, and said nut and said nut head being relatively thin.

5. The bone nail of claim 4, wherein a major portion of said screw shank is smooth.

6. The bone nail of claim 4, wherein said screw shank is conically enlarged towards screw said screw head, and said nut has a conical extension within which an inner thread is formed.

7. The bone nail of claim 4, wherein said screw shank and said screw head have an axial throughbore.

8. The bone nail of claim 1, wherein all bone nails have a constant diameter and a constant length between said distal end and said second bend and have a different length between said proximal end and said bend second.

9. The supra condylus bone nail as set forth in claim 1 wherein said first and second parts have conical ends opposite said operatively coupled ends.

10. The supra condylus bone nail as set forth in claim 9 wherein said first and second part are cannulated.

11. The supra condylus bone nail as set forth in claim 1 wherein said operatively coupled ends of said first and second parts have mating threads formed thereon.

12. A method of repairing a fracture in the condylus area of a femur bone comprising:

(a) bending the knee and laterally displacing the patella;

(b) drilling a bore which ends at the distal end of a femur between the conylii, which follows the intramedullary canal, and which is located remote from the sliding areas of the conylii on the plateau of the tibia in a plane parallel to the sagittal plane of the human body;

(c) driving a supra condylus bone nail into said bore of stem (b), wherein the bone nail is made of body-compatible material having an elongated shank with distal portion and a distal end and a proximal portion and a proximal end sized and configured to be inserted from the distal end of a femur from below the condylus, a first bend spaced from said distal end lying in a first parallel to the medial plane of the human body, and a second bend space d a greater distance from said distal end than said first bend and lying in said first plane, said proximal portion having at least one proximal transverse bore for a bone screw and said distal portion having at least one distal transverse bore located between said distal end and said first bend and inserting a condylus screw having a first part and a second part into the condylus in a medial-lateral direction from a first side thereof, said first part having length sufficient to extend through the distal transverse bore in said nail, and inserting said second part into said condylus in a medial-lateral direction from a second side thereof and operatively coupling ends of said first and second parts in a manner to compress the fracture in the condylus area of the bone.

* * * * *

UNITED STATES PATENT AND TRADEMARK OFFICE
CERTIFICATE OF CORRECTION

PATENT NO. : 6,010,505
DATED : January 4, 2000
INVENTOR(S) : Asche et al.

It is certified that error appears in the above-identified patent and that said Letters Patent is hereby corrected as shown below:

On the title page :

In the "Inventors" section, "Gernot Asche; Hans Erich Harder; Thomas Heinrich Anton Heinz; Klaus Hornberger; Reinhard Schnettler; Vilmos Vécsei, all of New York, N.Y." should read: -- Gernot Asche, Fed. Rep. Germany; Hans Erich Harder, Fed. Rep. Germany; Thomas Heinrich Anton Heinz, Vienna, Austria; Klaus Hornberger, Fed. Rep. Germany; Reinhard Schnettler, Fed. Rep. Germany; Vilmos Vécsei, Vienna, Austria. --

Column 4, line 7, cancel "screw" (first occurrence).
Column 4, line 15, "said bend second" should read -- said second bend --.
Column 4, line 40, "space d" should read -- spaced --.

Signed and Sealed this

Third Day of April, 2001

Attest:

NICHOLAS P. GODICI

*Attesting Officer*   *Acting Director of the United States Patent and Trademark Office*

UNITED STATES PATENT AND TRADEMARK OFFICE
CERTIFICATE OF CORRECTION

PATENT NO. : 6,010,505
DATED : January 4, 2000
INVENTOR(S) : Asche et al.

It is certified that error appears in the above-identified patent and that said Letters Patent is hereby corrected as shown below:

Column 2,
Line 59, "a" should read -- an --.

Column 3,
Line 32, after "with", insert -- a --.
Line 37, "medical" should read -- medial --.
Line 44, after "bend", insert -- , --.
Line 57, cancel "a" (first occurrence).

Column 4,
Line 36, before "distal" (first occurrence), insert -- a --.

Signed and Sealed this

Seventeenth Day of December, 2002

JAMES E. ROGAN
*Director of the United States Patent and Trademark Office*